(12) United States Patent
Yanagita

(10) Patent No.: US 6,852,692 B1
(45) Date of Patent: Feb. 8, 2005

(54) COMPOSITION FOR PROMOTING PASSIVE EXTENSION OF BLADDER SMOOTH MUSCLE

(75) Inventor: Toshihiko Yanagita, Mayazaki (JP)

(73) Assignee: Shionogi & Co., Ltd. (JP)

( * ) Notice: Subject to any disclaimer, the term of this patent is extended or adjusted under 35 U.S.C. 154(b) by 16 days.

(21) Appl. No.: 10/018,924

(22) PCT Filed: Jun. 23, 2000

(86) PCT No.: PCT/JP00/04166

§ 371 (c)(1),
(2), (4) Date: Dec. 19, 2001

(87) PCT Pub. No.: WO00/78338

PCT Pub. Date: Dec. 28, 2000

(30) Foreign Application Priority Data

Jun. 23, 1999 (JP) ............................................. 11-177549

(51) Int. Cl.$^7$ ............................................... A61K 38/00
(52) U.S. Cl. ........................................................ 514/12
(58) Field of Search ...................... 514/2, 44; 424/94.4; 530/300, 350, 399; 435/69.1, 320.1, 69.4, 6, 7.1; 536/23.5

(56) References Cited

U.S. PATENT DOCUMENTS

| | | |
|---|---|---|
| 5,639,855 A | 6/1997 | Kitamura et al. |
| 5,888,963 A | 3/1999 | Coy et al. |
| 5,910,416 A * | 6/1999 | Kitamura et al. ............. 435/7.1 |
| 2001/0041355 A1 * | 11/2001 | Ramakrishnan ............ 435/69.4 |
| 2002/0164707 A1 * | 11/2002 | Adamou et al. ........... 435/69.1 |

OTHER PUBLICATIONS

Israel, Anita and Diaz, Emilia, "*Diuretic and natriuretic action of adrenomedullin administered intracerebroventricularly in conscious rats,*" Regulatory Peptides 89 (2000) 13–18.

Junji Nishimura et al, "The relaxant effect of adrenomedullin on particular smooth muscles despite a general expression of its mRNA in smooth muscle, endothelial and epithelial", Br. J. Pharmacol. (1997), vol. 120, No. 2, pp. 193–200.

* cited by examiner

Primary Examiner—Karen Cochrane Carlson
Assistant Examiner—Sheridan Snedden
(74) Attorney, Agent, or Firm—Richard M. Klein; Fay, Sharpe, Fagan, Minnich & McKee, LLP

(57) ABSTRACT

A composition for promoting extension of bladder smooth muscle, comprising adrenomedullin. The composition of the present invention may be used to ameliorate a urination disorder. The urination disorder may be a urinary incontinence selected from the group consisting of urge incontinence, reflex incontinence, and overflow incontinence. According to the present invention, a method is provided for ameliorating a urination disorder using a composition comprising adrenomedullin. Further, use of adrenomedullin in production of a drug for ameliorating a urination disorder is provided.

22 Claims, 3 Drawing Sheets

FIG. 4

```
 1                                                      10
Tyr-Arg-Gln-Ser-Met-Asn-Asn-Phe-Gln-Gly-Leu-Arg-Ser-Phe-Gly-
├─RE1─┤ ├─────────────RE2─────────────┤ ├────RE3────
                                         ├──────────

20                                          30
Cys-Arg-Phe-Gly-Thr-Cys-Thr-Val-Gln-Lys-Leu-Ala-His-Gln-Ile-
├────┤ ├────────────────────────────────────RE4──────

40
Tyr-Gln-Phe-Thr-Asp-Lys-Asp-Lys-Asp-Asn-Val-Ala-Pro-Arg-Ser-
─────────────────────────────────────────────────────┤ ├──
─────────RE5─────────────────────────────────────────┤

50      52
Lys-Ile-Ser-Pro-Gln-Gly-Tyr-NH2
────────RE6────────────┤
```

COMPOSITION FOR PROMOTING PASSIVE EXTENSION OF BLADDER SMOOTH MUSCLE

TECHNICAL FIELD

The present invention relates to a composition for promoting extension of smooth muscle of the urinary bladder, comprising adrenomedullin.

BACKGROUND ART

Urinary incontinence is a common but very severe condition which mostly causes patients to be embarrassed, encounter difficulties, and be driven to despair. Clearly, there is a strong demand for a reliable and safe method of treating urinary incontinence. To date such a demand has not been satisfied to an appropriate level.

Urinary incontinence refers to a condition in which urine involuntarily flows out during the storage phase, and which is caused when there is a functional or organic abnormality in one or both of the urinary bladder and the urethra. Urinary incontinence occurs when bladder smooth muscle is involuntarily contracted so that the internal pressure of the urinary bladder is increased, or when urethral closure pressure created by the urethral sphincter and a supporting tissue surrounding the urethra is too weak to repel the internal pressure of the normal urinary bladder. Urinary incontinence is divided into several types depending on the pathology. Broad types are: urge incontinence; reflex incontinence; overflow incontinence (poorly compliant bladder), stress incontinence, total incontinence; and nocturnal enuresis.

Urge incontinence is a condition in which urine involuntarily flows out accompanying a strong urge to urinate, or after feeling an urge to urinate, a patient cannot resist urine outflow and wets before reaching a toilet. These are divided into motor and sensory types. Motor urge incontinence is caused by a disorder of an inhibitory pathway for the micturition reflex, or excitation of an exitatory pathway, a representative example of which is neurogenic bladder due to a lesion, such as for example a cerebrovascular disorder and a brain tumor. Representative examples of sensory urge incontinence include cystitis and urethritis.

Reflex incontinence is a condition in which when the urinary bladder is filled with urine to some extent without a normal urge to urinate, the urinary bladder is reflectively contracted, so that urine involuntarily flows out. Reflex incontinence includes neurogenic bladder due to injury of the spinal cord above the urination center in the sacral spinal cord, urinary incontinence of infants, and the like.

Overflow incontinence is a condition in which since urine cannot be sufficiently excreted, the urinary bladder is excessively filled with urine and the urine gradually flows out. Overflow incontinence includes neurogenic bladder (poorly compliant bladder) due to injury of peripheral nerves, and disorders of the passage of the lower urinary tract due to prostatic hypertrophy or cancer.

Stress incontinence is a symptom in which when a patient strains in sneezing or coughing, laughs, runs, or the like, so that abdominal pressure is rapidly increased, urine flows out without contraction of the urinary bladder. The increase in the abdominal pressure leads to a raise in the internal pressure of the urinary bladder. In this case, if the increased internal pressure exceeds the urethral closure pressure, urine flows out. Females more often suffer from this disorder. A major cause of stress incontinence is that supporting tissues surrounding the urethra are seriously weakened by parturition or aging, so that urethral closure pressure cannot be sufficiently generated.

Total incontinence is a condition characterized by dysfunction of the urethral sphincter, and in which urine flows out from the urethra at all times irrespective of the presence or absence of abdominal pressure. The cause of total incontinence is injury of the urethral sphincter caused by trauma of the pelvis or surgery of the prostate.

Nocturnal enuresis is also called bed-wetting, which is a condition in which patients of 4 or more years old, which is the age at which the habit of urinating is established, unconsciously void urine during sleep though they do not have an organic abnormality in the urinary tract or the nerve system and can urinate normally (no urinary incontinence) on awakening. This disorder is caused by the premature inhibitory mechanism of the central nerve system for the micturition reflex.

At present, anticholinergic agents are generally used for treatment of the following patients having urine storage disorders: (1) neurogenic bladder patients who have urinary incontinence due to the hyperactivity of urinary bladder and involuntarily urinate; (2) neurogenic bladder patients who do not have abnormal urinary bladder contraction but have a poorly compliant urinary bladder in which the internal pressure of the urinary bladder gradually increased as urine is filled; (3) one subset of patients who chiefly complain of pollakiuria; etc. Clinically, despite the efficacy of anticholinergic agents against urine storage disorders, when the anticholinergic agents are actually used, urinary bladder contraction is inhibited in urination so that urination disorders are often exacerbated to cause side effects, such as increased residual urine and anuresis.

As described above, clearly, urinary incontinence is one of today's major diseases, but current therapeutic methods are not satisfactory. There is a demand for a novel drug for treating urinary incontinence. The term "urination disorder" as used herein refers to an abnormal urination condition, such as urinary incontinence, caused by insufficient extension of bladder smooth muscle. Examples of urination disorders include urinary incontinence (e.g., urge incontinence), frequent urination, nocturnal pollakiuria. An agent capable of promoting extension of bladder smooth muscle would be expected to help bladder smooth muscle extend during storage phase to reduce the internal pressure of the urinary bladder. Thus, such an agent would be considered to be useful as drugs for treatment of urinary incontinence and other symptoms relating to urination.

It has been known that adrenomedullin has a vasodilatory action. For example, Nakamura et al., Jpn. J. Pharmacol. 67, 259–262 (1995) has reported in FIG. 1 that contracted mesenteric artery is extended by addition of adrenomedullin in a concentration-dependent manner. However, vasodilation cannot be considered to be identical with passive extension of muscle of the urinary bladder. For example, Nishimura et al., British J. Pharmacology, 120, 193–200 (1997) describes in FIG. 6 that addition of adrenomedullin to the urinary bladder does not cause contraction or extension (active extension) of the urinary bladder.

The present invention is intended to solve the above-described problems. The objective of the present invention is to provide a novel agent for promoting passive extension of bladder smooth muscle.

DISCLOSURE OF THE INVENTION

The inventions found that adrenomedullin originally identified as a peptide having a hypotensive action does not directly extend bladder smooth muscle, but has an action of promoting passive extension of the urinary bladder wall due to urine storage (i.e., an action of promoting extension of bladder smooth muscle) and based on that finding, completed the present invention.

Adrenomedullin does not inhibit contraction of the urinary bladder due to acetylcholine (i.e., urinary bladder contraction in urination) and therefore, can provide a therapeutic agent for ameliorating a urine storage disorder without inhibiting urinary bladder contraction in urination and substantially without side effects.

A composition of the present invention for promoting passive extension of bladder smooth muscle comprises adrenomedullin. The composition may be used to ameliorate a urination disorder. The urination disorder may be a urinary incontinence selected from the group consisting of urge incontinence, reflex incontinence, and overflow incontinence.

In one embodiment, the adrenomedullin may be any of the following peptides: (a) a petpide comprising an amino acid sequence from Ser in position 13 to Tyr in position 52 of SEQ ID NO: 2 in SEQUENCE LISTING; (b) a peptide comprising an amino acid sequence having one or several amino acid deleted, substituted, or added in the amino acid sequence (a), and having an action of promoting extension of bladder smooth muscle; (c) a petpide comprising an amino acid sequence from Tyr in position 1 to Tyr in position 52 of SEQ ID NO: 2 in SEQUENCE LISTING; (d) a peptide comprising an amino acid sequence having one or several amino acid deleted, substituted, or added in the amino acid sequence (c), and having an action of promoting extension of bladder smooth muscle; (e) a petpide comprising an amino acid sequence from Ala in position −73 to Tyr in position 52 of SEQ ID NO: 2 in SEQUENCE LISTING; (f) a peptide comprising an amino acid sequence having one or several amino acid deleted, substituted, or added in the amino acid sequence (e), and having an action of promoting extension of bladder smooth muscle; (g) a petpide comprising an amino acid sequence from Met in position −94 to Leu in position 91 of SEQ ID NO: 2 in SEQUENCE LISTING; and (h) a peptide comprising an amino acid sequence having one or several amino acid deleted, substituted, or added in the amino acid sequence (g), and having an action of promoting extension of bladder smooth muscle.

In another embodiment, the C-terminus of the adrenomedullin may be amidated. Gly may be added to the C-terminus of the adrenomedullin.

In another embodiment, in the adrenomedullin, Cys in position 16 and Cys in position 21 of SEQ ID NO: 2 in SEQUENCE LISTING may be crosslinked. The crosslink may be a disulfide bond or a —$CH_2$—$CH_2$— bond.

A method of the present invention for ameliorating a urination disorder uses a composition comprising adrenomedullin.

The present invention also provides use of adrenomedullin in production of a drug for ameliorating a urination disorder.

BRIEF DESCRIPTION OF THE DRAWINGS

As shown in FIG. 1(a), ends of the urinary bladder were cut off along solid lines, and the urinary bladder was cut open along dashed lines. Four urinary bladder sections were obtained from the cut-open urinary bladder along three solid lines as shown in FIG. 1(b).

FIG. 4 is a diagram showing the amino acid sequence of adrenomedullin derived from human pheochromocytoma. This sequence comprises the amino acid sequence from Tyr in position 1 to Tyr in position 52 of SEQ ID NO: 2 in SEQUENCE LISTING RE1 to RE6 indicate fragments produced by digesting the amino acid sequence with arginylendopeptidase.

BEST MODE FOR CARRYING OUT THE INVENTION

Figure 1:
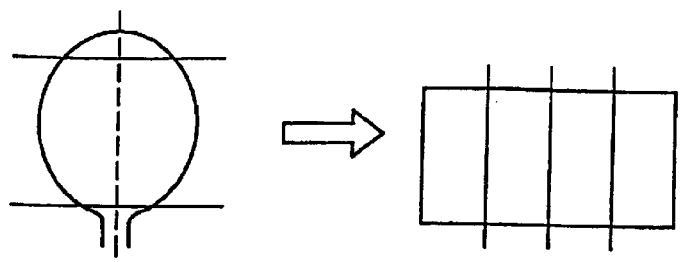
FIG. 1 is a schematic diagram showing a method for dissecting the urinary bladder.

When carrying out the present invention, protein separation and analysis methods, recombinant DNA techniques, and assays, which are known in the art, may be employed unless otherwise specified.

I. Definition

Hereinafter, the terms used herein to explain the present invention will be described.

An "adrenomedullin" is a peptide having a hypotensive action, originally isolated from human pheochromocytoma. The term "adrenomedullin" as used herein is not limited to the particular peptide, but includes peptides having substantial homology in the amino acid sequence with that peptide. Examples of the homologous peptides include species mutants and allelic mutants. Human-derived adrenomedullin comprises an amino acid sequence from Tyr in position 1 to Tyr in position 52 of SEQ ID NO: 2 in SEQUENCE LISTING. (The peptide consisting of an amino acid sequence from Met in position −94 to Leu in position 91 of SEQ ID NO: 2 in SEQUENCE LISTING is believed to be preproadrenomedullin. The peptide obtained by processing of a signal peptide and consisting of an amino acid sequence from Ala in position −73 to Leu in position 91 of SEQ ID NO: 2 in SEQUENCE LISTING is believed to be proadrenomedullin. The peptide consists of an amino acid sequence from Ser in position 13 to Tyr in position 52 of SEQ ID NO: 2 in SEQUENCE LISTING is an adrenomedullin fragment which has been confirmed to have a hypotensive action. Adrenomedullin in any of the above-described forms may be employed in the present invention.) Human-derived adrenomedullin may be encoded by a polynucleotide sequence from T in position 447 to C in position 602 of SEQ ID NO: 1 in SEQUENCE LISTING.

Porcine-derived adrenomedullin comprises an amino acid sequence from Tyr in position 1 to Tyr in position 52 of SEQ ID NO: 4 in SEQUENCE LISTING. Porcine-derived adrenomedullin may be encoded by a polynucleotide sequence from T in position 430 to C in position 585 of SEQ ID NO: 3 in SEQUENCE LISTING. Rat-derived adrenomedullin comprises an amino acid sequence from Tyr in position 1 to Tyr in position 50 of SEQ ID NO: 6 in SEQUENCE LISTING. Rat-derived adrenomedullin may be encoded by a polynucleotide sequence from T in position 433 to T in position 582 of SEQ ID NO: 5 in SEQUENCE LISTING.

Clearly, human-derived peptides are preferable for human diseases or treatment of a human. However, homologous peptides derived from other mammals may also be employed for some purposes. Further, comparison of human-derived peptides with peptides derived from other mammals is important when an attempt is made to obtain a variant maintaining a desired activity of a human-derived peptide.

Adrenomedullin used in the present invention is not necessarily limited to the above-described sequences, but includes, as subjects, homologous peptides having an amino acid sequence which has one or several amino acid deleted, substituted, or added in the above-described sequences and maintaining a desired activity.

Amino acid conservative substitution is one preferable means for obtaining homologous peptides. Conservative substitution representatively includes substitutions conducted within the following groups: glycine, alanine; valine, isoleucine, leucine; aspartic acid, glutamic acid; asparagine, glutamine; serine, threonine; lysine, arginine; and phenylalanine, tyrosine.

The homology between two amino acid sequences is determined by optionally introducing a gap to optimize residue matching. A peptide having an amino acid sequence, which has substantially homology with the amino acid sequence of human adrenomedullin, has representatively about 60% homology with the amino acid sequence of human adrenomedullin, preferably at least about 70%, more preferably at least about 80%, and in an especially preferable embodiment, at least about 90% or more. Software for determining homology is easily available.

In the present invention, a peptide is by definition referred to have an action of promoting extension of bladder smooth muscle if the degree of extention of the urinary bladder is about 80% or more and preferably about 90% or more of the value indicated in the experimental sample of Example 1 described below when measured under substantially the same conditions as those of Example 1 below.

The C-terminus of a peptide used in the present invention may or may not be amidated. "Amidation of C-terminus" refers to one of modification reactions of a peptide, in which the COOH group of the C-terminal amino acid of a peptide is changed to the form of $CONH_2$. A number of biologically active peptides functioning in vivo are first biosynthesized as a precursor protein having a larger molecular weight. The precursor protein is then matured by a modification reaction such as for example the amidation of the C-terminus. The amidation is conducted by a C-terminal amidating enzyme acting on the precursor protein. The precursor protein always includes a Gly residue on the C-terminal side of a residue to be amidated, which is frequently followed by a basic amino acid sequence pair, such as for example Lys-Arg or Arg-Arg, on the C-terminal side (Mizuno, Seikagaku, Vol. 61, No. 12, pp. 1435–1461 (1989)).

II. Adrenomedullin Having an Action of Promoting Extension of Bladder Smooth Muscle In the present invention, adrenomedullin is utilized as an effective component of a composition for promoting extension of bladder smooth muscle. Adrenomedullin is utilized as an effective component for manufacturing a drug for ameliorating a urination disorder. Adrenomedullin may be isolated from naturally-occurring sources, produced using recombinant DNA techniques, or chemically synthesized.

When adrenomedullin is isolated from naturally-occurring sources, purification may be conducted, for example, in the following way. For example, firstly human pheochromocytoma is pulverized to obtain a crude extract which is in turn subjected to various chromatography techniques for purification. In this case, by monitoring an increase in the cAMP activity of platelets, a fraction containing adrenomedullin of interest can be obtained. Method for isolation and purification of adrenomedullin are described in Japanese Laid-Open Publication No. 7-196693.

When adrenomedullin is produced using recombinant DNA techniques, the DNA sequence encoding a peptide of interest is expressed using various recombinant systems. Construction of expression vectors and preparation of transformants having appropriate DNA sequences are conducted by methods known in the art. Expression may be conducted using prokaryote systems or eukaryote systems.

Prokaryote hosts used include *E. coli, bacillus*, and other bacteria. For such prokaryote hosts, plasmid vectors having replication sites and control sequences compatible with the hosts are used. For example, *E. coli* is typically transformed with a derivative of pBR322 which is a plasmid derived from *E. coli*. The control sequence herein is defined to include a promoter for initiation of transcription, an operator if necessary, and a ribosome binding site. Such a control sequence includes generally used promoters such as for example β-lactamase and lactose promoter systems (Chang et al., Nature (1977) 198, 1056), tryptophan promoters (Goeddel et al., Nucleic Acids Res., (1980) 8: 4057), and $P_L$ promoters derived from λ and N-gene ribosome binding sites (Shimatake, Nature (1981) 292, 128).

As a eukaryote host, yeast is used, for example. For such a host eukaryote, a plasmid vector having a replication site and a control sequence compatible with the host is used. For example, yeast is transformed with pYEUra3 (Clontech). Other promoters useful in a yeast host include, for example, promoter classes for synthesizing a glycolytic enzyme, such as for example a promoter for 3-phosphoglycerate kinase (Hitzeman et al., J. Biol. Chem. (1980) 255, 2073). Other promoters include those derived from an enolase gene or those derived from a Leu2 gene obtained from YEp13.

Appropriate mammalian promoters include metallothionein, an early or late promoter derived from SV40, and other virus promoters such as for example those derived from polyoma virus, adenovirus II, bovine papilloma virus and avian sarcoma virus.

A transformant can be obtained by introducing an expression vector into an appropriate host cell. A desired adrenomedullin can be obtained by culturing the transformant under appropriate conditions.

Chemical synthesis of adrenomedullin may be conducted within a method known in the art. For example, adrenomedullin may be synthesized by a solid phase method using a peptide synthesizer. A C-terminal amidated peptide can be synthesized on a peptide synthesizer by condensing amino acids sequentially from the C-terminal amino acid to the N-terminal amino acid using a benzhydryl amine resin and a standard DCC/HOBt, and cutting out an intended peptide from the resultant peptide resin by a standard cleavage method (trifluoromethanesulfonic acid method).

A C-terminal amidated adrenomedullin may be obtained by one of the following: a carboxyl group at the C-terminus of the peptide obtained by expression in a host is chemically amidated; or a peptide is prepared so as to have Gly added to the C-terminus of an intended amino acid sequence, and is then allowed to react with the above-mentioned C-terminal amidating enzyme for amidation.

Alternatively, the peptide obtained by adding Gly to the C-terminus of adrenomedullin may be amidated due to an action of a C-terminal amidating enzyme in vivo as described above.

A disulfide bond can be formed, for example, by oxidizing a peptide by air oxidization or with an appropriate oxidant. The substitution of the disulfide bond can be conducted with a —$CH_2$—$CH_2$— bond by a well-known method (O. Keller et al., Helv. Chim. Acta (1974) 57: 1253). Generally, cleavage in the disulfide bond is avoided by substituting a —$CH_2$—$CH_2$— bond for the disulfide bond, resulting in stabilization of the protein.

Assay methods for action of promoting extension of bladder smooth muscle, which are known in the art, may be used to confirm that the thus-obtained adrenomedullin has an action of promoting extension of bladder smooth muscle. Examples of such assays include a method employing the urinary bladder isolated from any animal, and a method of measuring the internal pressure of the urinary bladder under anesthetization. When the urinary bladder isolated from a rat is used, for example, action of promoting extension of bladder smooth muscle may be assayed under the following conditions. The urinary bladder is isolated from a rat and cut into several pieces to obtain urinary bladder strips. While the resultant urinary bladder strips are immersed in a buffer solution, such as for example Tyrode's solution, extension or contraction of the urinary bladder is continuously examined using a measuring apparatus, such as for example an isometric transducer and an isotonic transducer. The urinary bladder is allowed to be extended in the presence or absence of a subject peptide, and extension of the urinary bladder is compared between the two cases to judge whether or not the peptide has an action of promoting extension of bladder smooth muscle.

III. Preparation of a Composition for Promoting Extension of Bladder Smooth Muscle A composition of the present invention comprises an effective amount of adrenomedullin and may further comprise any excipient known to those skilled in the art. Examples of the excipients include lactose, cornstarch, magnesium stearate, and alum.

The composition of the present invention is prepared in accordance with methods known in the art.

The composition of the present invention may be in any form. The composition of the present invention may be a solid, such as for example a tablet, a pill, a capsule, and a granule; or a liquid, such as for example an aqueous solution and a suspension. When the composition of the present invention is orally administered as a tablet, an excipient, such as for example lactose, cornstarch, and magnesium stearate, may be commonly used. When the composition of the present invention is orally administered as a capsule, an excipient, such as for example lactose and dried cornstarch, may be commonly used. In order to orally administer adrenomedullin as an aqueous suspension, the adrenomedullin may be used in combination with an emulsion or a suspension. The aqueous suspension may optionally contain a sweetner and an aroma chemical. When the composition of the present invention is intramuscularly, intraperitoneally, subcutaneously, or intravenously injected, adrenomedullin is dissolved in a sterilized solution to prepare a buffer solution which is in turn adjusted into an appropriate pH. When the composition of the present invention is intravenously administered, the composition is preferably isotonic.

The composition of the present invention may be used as a drug for ameliorating a urination disorder.

IV. Administration of a Composition for Promoting Extension of Bladder Smooth Muscle The composition of the present invention may be administered in the form of a conventional peptide formulation as described in Remington's Pharmaceutical Sciences, Mack Publishing, Easton, Pa. For example, the composition of the present invention may be administered orally, or alternatively parenterally, such as for example intravenous administration, intramuscular injection, intraperitoneal injection, and subcutaneous injection. The peptide may be administered by injection into the urinary bladder.

When the composition of the present invention is administered into a human subject, typically, the dose per day can be appropriately determined by those skilled in the art by taking into consideration a patient's symptoms, severity, individual differences in sensitivity, weight, age, and the like. The composition of the present invention may be administered once a day or several times a day.

Urination disorders would be ameliorated by administration of the composition of the present invention.

EXAMPLES

Hereinafter, the action of adrenomedullin of the present invention as a drug for promoting extension of bladder smooth muscle will be more specifically described. The present invention is not limited to the following examples. Adrenomedullin used in the examples is a synthesized peptide consisting of an amino acid sequence from Tyr in position 1 to Tyr in position 50 of SEQ ID NO: 6 (available from Peptide Institute, Inc.).

Example 1

Effect of Adrenomedullin on Extension of the Urinary Bladder of a Male Rat 8 to 16 weeks old male rats were sacrificed by hammering their heads. Thereafter, the rats were decapitated, followed by exsanguination. The urinary bladders were isolated from the rats. Each isolated urinary bladder was cut into four portions, thereby obtaining urinary bladder strips (FIG. 1).

The effect of adrenomedullin on the rat urinary bladder was examined by measuring contractions of the urinary bladder strips using an isotonic transducer TD-112S (manufactured Nippon Kohden Corporation) where the tension was 1 g.

The urinary bladder strips were firstly immersed in 30 ml of Tyrode's solution with 100 nM adrenomedullin (experimental sample) or without it (control sample). In this situation, the sections were attached to the isometric transducer where the tension was 1 g, to continuously measure relaxation of the urinary bladder. The composition of the Tyrode's solution is as follows: 139 mM NaCl, 2.7 mM KCl, 11.9 mM $NaHCO_3$, 2.6 mM $MgCl_2.6H_2O$, 0.4 mM $NaH_2PO_4.2H_2O$, 1.7 mM $CaCl_2$, and 5.5 mM glucose; pH 7.4).

Figure 2:
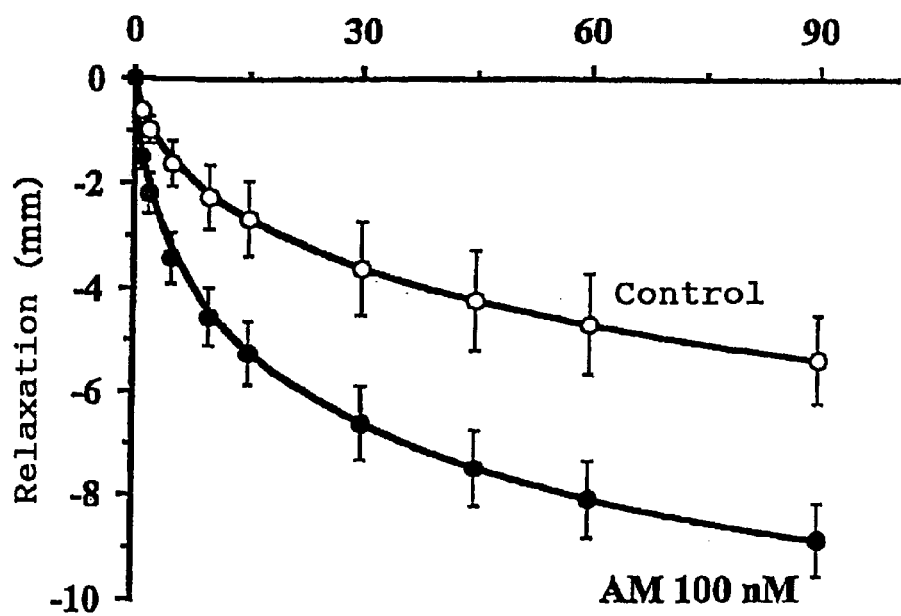
FIG. 2 is a graph showing the results of measurement of the effect of adrenomedullin on extension of the urinary bladder where the applied tension is 1 g. White circles indicate controls, while black circles indicate the case of addition of adrenomedullin.

The above-described experiment was repeated five times. The results are shown in FIG. 2. Solid colored circles indicate the results of the experimental sample, while plain circles indicate averages of the control sample. Vertical bars indicate the standard deviation of a two-way analysis of variance. The vertical axis indicates the length of relaxation (mm), while the horizontal axis indicate time (minutes).

As shown in FIG. 2, when tension was applied to the urinary bladder in the presence of adrenomedullin to cause the urinary bladder to be extended, the result obtained is that the urinary bladder wall was more extended compared to the case of the absence of adrenomedullin. Normally, the urinary bladder is passively extended by urine filling therein during the urine storage phase, and the extension prevents the internal pressure of the urinary bladder from being increased, so that the internal pressure of the urinary bladder remains at a constant low value. A high expansibility of the urinary bladder is referred to as a high level of compliance. As a result of this example, it was demonstrated that adrenomedullin causes the urinary bladder to remain in a higher compliance state during the urine storage phase, thereby increasing the capacity of the urinary bladder.

Example 2

Figure 3:
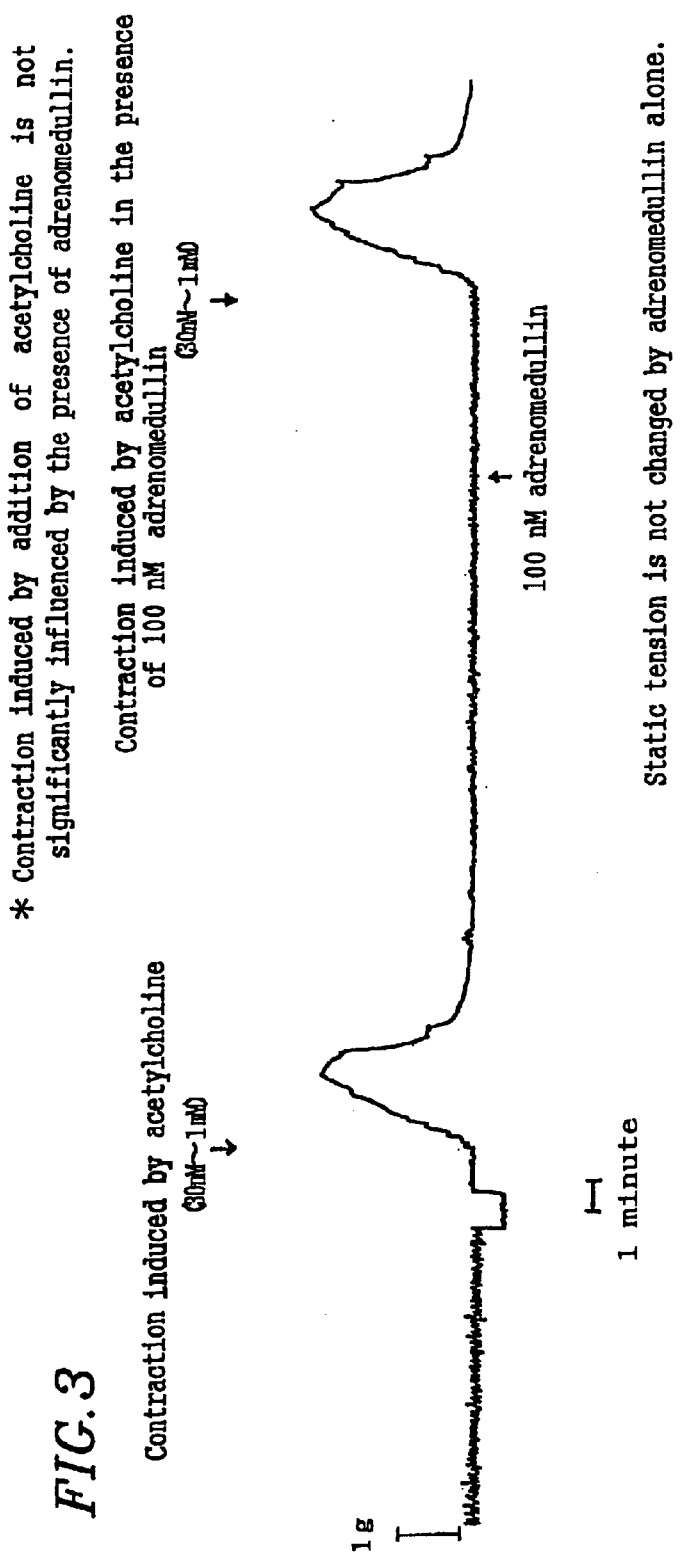
FIG. 3 is a graph showing the results of measurement of the effect of adrenomedullin on contraction of the urinary bladder due to acetylcholine.

Effect of Adrenomedullin on Static Tension, and Contraction Due to Acetylcholine of the Urinary Bladder of a Male Rat Urinary bladder strips were prepared in a manner similar to that of Example 1. The urinary bladder sections were attached to an isometric transducer FD pickup TB611T (manufactured by Nippon Kohden Corporation) in Tyrode's solution. Contraction of the urinary bladder was continuously measured. Firstly, 30 nM to 1 mM acetylcholine was added to the Tyrode's solution. As a result, contraction of the urinary bladder occurred (FIG. 3). In FIG. 3, the vertical axis indicates tension (unit: g), while the horizontal axis indicates time. Contraction induced by acetylcholine was confirmed, followed by washing out acetylcholine. Thereafter, 100 nM adrenomedullin was added to the Tyrode's solution. As a result, the urinary bladder was not contracted. Further, 30 nM to 1 mM acetylcholine was added to the Tyrode's solution. As a result, recontraction of the urinary bladder occured. The contraction induced by acetylcholine alone before the addition of adrenomedullin was not significantly different from the contraction induced by acetylcholine in the presence of adrenomedullin.

Therefore, the tested adrenomedullin did not affect the static tension of the urinary bladder, or exhibit an effect of preventing contraction of the urinary bladder due to acetylcholine, which is believed to correspond to contraction of the urinary bladder during a voiding phase.

INDUSTRIAL APPLICABILITY

According to the present invention, a composition for promoting extension of bladder smooth muscle, comprising adrenomedullin is provided. Such a composition is useful for ameliorating a urination disorder selected from the group consisting of urge incontinence, reflex incontinence, and overflow incontinence.

What is claimed is:

1. A method for ameliorating a urination disorder comprising administering a composition comprising adrenomedullin wherein the urination disorder is a urinary incontinence selected from the group consisting of urine incontinence, reflex incontinence, and overflow incontinence.

2. A method according to claim 1, wherein the adrenomedullin is:
   (a) a peptide comprising an amino acid sequence from Ser in position 13 to Tyr in position 52 of SEQ ID NO: 2 in SEQUENCE LISTING; or
   (b) a peptide comprising an amino acid sequence having at least about 80% identity with the amino acid sequence (a), and having an action of promoting extension of bladder smooth muscle.

3. A method according to claim 1, wherein the adrenomedullin is:
   (a) a peptide comprising an amino acid sequence from Tyr in position 1 to Tyr in position 52 of SEQ IS NO: 2 in SEQUENCE LISTING; or
   (b) a peptide comprising an amino acid sequence having at least about 80% identity with the amino acid sequence (a), and having an action of promoting extension of bladder smooth muscle.

4. A method according to claim 1, wherein the adrenomedullin is:
   (a) a peptide comprising an amino acid sequence from Ala in position −73 to Tyr in position 52 of SEQ ID NO: 2 in SEQUENCE LISTING; or
   (b) a peptide comprising an amino acid sequence having at least about 80% identity with the amino acid sequence (a), and having an action of promoting extension of bladder smooth muscle.

5. A method according to claim 1, wherein the adrenomedullin is:
   (a) a peptide comprising an amino acid sequence from Met in position −94 to Leu in position 91 of SEQ IS NO: 2 in SEQUENCE LISTING; or
   (b) a peptide comprising an amino acid sequence having at least about 80% identity with the amino acid sequence (a), and having an action of promoting extension of bladder smooth muscle.

6. A method according to claim 1, wherein the C-terminus of the adrenomedullin is amidated.

7. A method according to claim 1, wherein Gly is added to the C-terminus of the adrenomedullin.

8. A method according to claim 1, wherein in the adrenomedullin, Cys in position 16 and Cys in position 21 of SEQ ID NO: 2 in SEQUENCE LISTING are crosslinked.

9. A method according to claim 8, wherein the crosslink is a disulfide bond.

10. A method according to claim 8, wherein the crosslink is a —$CH_2$—$CH_2$— bond.

11. A method for promoting passive extension of bladder smooth muscle comprising administering a composition comprising adrenomedullin.

12. A method according to claim 11, wherein the adrenomedullin is:
   a peptide comprising an amino acid sequence from Ser in position 13 to Tyr in position 52 of SEQ ID NO: 2 in SEQUENCE LISTING; or
   a peptide comprising an amino acid sequence having at least about 80% identity with the amino acid sequence (a), and having an action of promoting extension of bladder smooth muscle.

13. A method according to claim 11, wherein the adrenomedullin is:
   (a) a peptide comprising an amino acid sequence from Tyr in position 1 to Tyr in position 52 of SEQ ID NO: 2 in SEQUENCE LISTING; or
   (b) a peptide comprising an amino acid sequence having at least about 80% identity with the amino acid sequence (a), and having an action of promoting extension of bladder smooth muscle.

14. A method according to claim 11, wherein the adrenomedullin is:
   (a) a peptide comprising an amino acid sequence from Ala in position −73 to Tyr in position 52 of SEQ ID NO: 2 in SEQUENCE LISTING; or
   (b) a peptide comprising an amino acid sequence having at least about 80% identity with the amino acid sequence (a), and having an action of promoting extension of bladder smooth muscle.

15. A method according to claim 11, wherein the adrenomedullin is:
   (a) a peptide comprising an amino acid sequence from Met in position −94 to Leu in position 91 of SEQ ID NO: 2 in SEQUENCE LISTING; or
   (b) a peptide comprising an amino acid sequence having at least about 80% identity with the amino acid sequence (a), and having an action of promoting extension of bladder smooth muscle.

16. A method according to claim 11, wherein the C-terminus of the adrenomedullin is amidated.

17. A method according to claim 11, wherein Gly is added to the C-terminus of the adrenomedullin.

18. A method according to claim 11, wherein in the adrenomedullin, Cys in position 16 and Cys in position 21 of SEQ ID NO: 2 in SEQUENCE LISTING are crosslinked.

19. A method according to claim 18, wherein the crosslink is a disulfide bond.

20. A method according to claim 18, wherein the crosslink is a —$CH_2$—$CH_2$— bond.

21. A method according to claim 11, whereby a urination disorder is ameliorated.

22. A method according to claim 21, wherein the urination disorder is a urinary incontinence selected from the group consisting of urge incontinence, reflex incontinence, and overflow incontinence.

* * * * *

SEQUENCE LISTING

<160> NUMBER OF SEQ ID NOS: 6

<210> SEQ ID NO 1
<211> LENGTH: 1457
<212> TYPE: DNA
<213> ORGANISM: Homo sapiens
<220> FEATURE:
<221> NAME/KEY: CDS
<222> LOCATION: (165)..(719)
<221> NAME/KEY: mat peptide
<222> LOCATION: (447)..(602)

<400> SEQUENCE: 1

```
ggcacgagct ggatagaaca gctcaagcct tgccacttcg ggcttctcac tgcagctggg      60
cttggacttc ggagttttgc cattgccagt gggacgtctg agactttctc cttcaagtac     120
ttggcagatc actctcttag cagggtctgc gcttcgcagc cggg atg aag ctg gtt     176
                                                  Met Lys Leu Val tcc gtc gcc ctg atg tac ctg ggt tcg ctc gcc ttc cta ggc gct gac      224
Ser Val Ala Leu Met Tyr Leu Gly Ser Leu Ala Phe Leu Gly Ala Asp
-90                 -85                 -80                 -75 acc gct cgg ttg gat gtc gcg tcg gag ttt cga aag aag tgg aat aag      272
Thr Ala Arg Leu Asp Val Ala Ser Glu Phe Arg Lys Lys Trp Asn Lys
            -70                 -65                 -60 tgg gct ctg agt cgt ggg aag agg gaa ctg cgg atg tcc agc agc tac      320
Trp Ala Leu Ser Arg Gly Lys Arg Glu Leu Arg Met Ser Ser Ser Tyr
        -55                 -50                 -45 ccc acc ggg ctc gct gac gtg aag gcc ggg cct gcc cag acc ctt att      368
Pro Thr Gly Leu Ala Asp Val Lys Ala Gly Pro Ala Gln Thr Leu Ile
    -40                 -35                 -30 cgg ccc cag gac atg aag ggt gcc tct cga agc ccc gaa gac agc agt      416
Arg Pro Gln Asp Met Lys Gly Ala Ser Arg Ser Pro Glu Asp Ser Ser
-25                 -20                 -15 ccg gat gcc gcc cgc atc cga gtc aag cgc tac cgc cag agc atg aac      464
Pro Asp Ala Ala Arg Ile Arg Val Lys Arg Tyr Arg Gln Ser Met Asn
-10                  -5                  -1   1                 5 aac ttc cag ggc ctc cgg agc ttt ggc tgc cgc ttc ggg acg tgc acg      512
Asn Phe Gln Gly Leu Arg Ser Phe Gly Cys Arg Phe Gly Thr Cys Thr
                10                  15                  20 gtg cag aag ctg gca cac cag atc tac cag ttc aca gat aag gac aag      560
Val Gln Lys Leu Ala His Gln Ile Tyr Gln Phe Thr Asp Lys Asp Lys
            25                  30                  35 gac aac gtc gcc ccc agg agc aag atc agc ccc cag ggc tac ggc cgc      608
Asp Asn Val Ala Pro Arg Ser Lys Ile Ser Pro Gln Gly Tyr Gly Arg
        40                  45                  50
```

-continued

```
cgg cgc cgg cgc tcc ctg ccc gag gcc ggc ccg ggt cgg act ctg gtg      656
Arg Arg Arg Arg Ser Leu Pro Glu Ala Gly Pro Gly Arg Thr Leu Val
 55              60                  65                  70 tct tct aag cca caa gca cac ggg gct cca gcc ccc ccg agt gga agt      704
Ser Ser Lys Pro Gln Ala His Gly Ala Pro Ala Pro Pro Ser Gly Ser
                 75                  80                  85 gct ccc cac ttt ctt taggatttag gcgcccatgg tacaaggaat agtcgcgcaa      759
Ala Pro His Phe Leu
             90 gcatcccgct ggtgcctccc gggacgaagg acttcccgag cggtgtgggg accgggctct    819 gacagccctg cggagaccct gagtccggga ggcaccgtcc ggcggcgagc tctggctttg    879 caagggcccc tccttctggg ggcttcgctt ccttagcctt gctcaggtgc aagtgcccca    939 gggggcgggg tgcagaagaa tccgagtgtt tgccaggctt aaggagagga gaaactgaga    999 aatgaatgct gagaccccg gagcaggggt ctgagccaca gccgtgctcg cccacaaact    1059 gatttctcac ggcgtgtcac cccaccaggg cgcaagcctc actattactt gaactttcca   1119 aaacctaaag aggaaaagtg caatgcgtgt tgtacataca gaggtaacta tcaatatttta   1179 agtttgttgc tgtcaagatt ttttttgtaa cttcaaatat agagatattt ttgtacgtta    1239 tatattgtat taagggcatt ttaaaagcaa ttatattgtc ctccctatt ttaagacgtg    1299 aatgtctcag cgaggtgtaa agttgttcgc cgcgtggaat gtgagtgtgt ttgtgtgcat    1359 gaaagagaaa gactgattac ctcctgtgtg gaagaaggaa acaccgagtc tctgtataat    1419 ctatttacat aaaatgggtg atatgcgaac agcaaacc                           1457
```

<210> SEQ ID NO 2
<211> LENGTH: 185
<212> TYPE: PRT
<213> ORGANISM: Homo sapiens

<400> SEQUENCE: 2

```
Met Lys Leu Val Ser Val Ala Leu Met Tyr Leu Gly Ser Leu Ala Phe
            -90                 -85                 -80

Leu Gly Ala Asp Thr Ala Arg Leu Asp Val Ala Ser Glu Phe Arg Lys
            -75                 -70                 -65

Lys Trp Asn Lys Trp Ala Leu Ser Arg Gly Lys Arg Glu Leu Arg Met
            -60                 -55                 -50

Ser Ser Ser Tyr Pro Thr Gly Leu Ala Asp Val Lys Ala Gly Pro Ala
            -45                 -40                 -35

Gln Thr Leu Ile Arg Pro Gln Asp Met Lys Gly Ala Ser Arg Ser Pro
-30                 -25                 -20                 -15

Glu Asp Ser Ser Pro Asp Ala Ala Arg Ile Arg Val Lys Arg Tyr Arg
            -10                 -5                  -1   1

Gln Ser Met Asn Asn Phe Gln Gly Leu Arg Ser Phe Gly Cys Arg Phe
              5                  10                  15

Gly Thr Cys Thr Val Gln Lys Leu Ala His Gln Ile Tyr Gln Phe Thr
             20                  25                  30

Asp Lys Asp Lys Asp Asn Val Ala Pro Arg Ser Lys Ile Ser Pro Gln
 35                  40                  45                  50

Gly Tyr Gly Arg Arg Arg Arg Ser Leu Pro Glu Ala Gly Pro Gly
                 55                  60                  65

Arg Thr Leu Val Ser Ser Lys Pro Gln Ala His Gly Ala Pro Ala Pro
             70                  75                  80

Pro Ser Gly Ser Ala Pro His Phe Leu
```

<210> SEQ ID NO 3
<211> LENGTH: 1493
<212> TYPE: DNA
<213> ORGANISM: Sus scrofa
<220> FEATURE:
<221> NAME/KEY: CDS
<222> LOCATION: (148)..(711)
<221> NAME/KEY: mat peptide
<222> LOCATION: (430)..(585)

<400> SEQUENCE: 3

```
gcggaacagc tcgagccttg ccacctctag tttcttacca cagcttggac gtcggggttt      60
tgccactgcc agagggacgt ctcagacttc atcttcccaa atcttggcag atcaccccct     120
tagcagggtc tgcacatctc agccggg atg aag ctg gtt ccc gta gcc ctc atg     174
                              Met Lys Leu Val Pro Val Ala Leu Met
                                                           -90 tac ctg ggc tcg ctc gcc ttc ctg ggc gct gac aca gct cgg ctc gac       222
Tyr Leu Gly Ser Leu Ala Phe Leu Gly Ala Asp Thr Ala Arg Leu Asp
-85                 -80                 -75                 -70 gtg gcg gca gag ttc cga aag aaa tgg aat aag tgg gct cta agt cgt       270
Val Ala Ala Glu Phe Arg Lys Lys Trp Asn Lys Trp Ala Leu Ser Arg
                -65                 -60                 -55 gga aaa aga gaa ctt cgg ctg tcc agc agc tac ccc acc ggg atc gcc       318
Gly Lys Arg Glu Leu Arg Leu Ser Ser Ser Tyr Pro Thr Gly Ile Ala
            -50                 -45                 -40 gac ttg aag gcc ggg cct gcc cag act gtc att cgg ccc cag gat gtg       366
Asp Leu Lys Ala Gly Pro Ala Gln Thr Val Ile Arg Pro Gln Asp Val
        -35                 -30                 -25 aag ggc tcc tct cgc agc ccc cag gcc agc att ccg gat gca gcc cgc       414
Lys Gly Ser Ser Arg Ser Pro Gln Ala Ser Ile Pro Asp Ala Ala Arg
    -20                 -15                 -10 atc cga gtc aag cgc tac cgc cag agt atg aac aac ttc cag ggc ctg       462
Ile Arg Val Lys Arg Tyr Arg Gln Ser Met Asn Asn Phe Gln Gly Leu
-5               -1   1                   5                  10 cgg agc ttc ggc tgt cgc ttt ggg acg tgc acc gtg cag aag ctg gcg       510
Arg Ser Phe Gly Cys Arg Phe Gly Thr Cys Thr Val Gln Lys Leu Ala
                 15                  20                  25 cac cag atc tac cag ttc acg gac aaa gac aag gac ggc gtc gcc ccc       558
His Gln Ile Tyr Gln Phe Thr Asp Lys Asp Lys Asp Gly Val Ala Pro
             30                  35                  40 cgg agc aag atc agc ccc cag ggc tac ggc cgc cgg cga cgc tct            606
Arg Ser Lys Ile Ser Pro Gln Gly Tyr Gly Arg Arg Arg Arg Ser
         45                  50                  55 ctg ccc gaa gcc agc ctg ggc cgg act ctg agg tcc cag gag cca cag       654
Leu Pro Glu Ala Ser Leu Gly Arg Thr Leu Arg Ser Gln Glu Pro Gln
60                  65                  70                  75 gcg cac ggg gcc ccg gcc tcc ccg gcg cat caa gtg ctc gcc act ctc       702
Ala His Gly Ala Pro Ala Ser Pro Ala His Gln Val Leu Ala Thr Leu
                 80                  85                  90 ttt agg att taggcgccta ctgtggcagc agcgaacagt cgcgcatgca              751
Phe Arg Ile tcatgccggc gcttcctggg gcgggggct tcccggagcc gagcccctca gcggctgggg      811
cccgggcaga gacagcattg agagaccgag agtccgggag gcacagacca gcggcgagcc     871
ctgcattttc aggaacccgt cctgcttgga ggcagtgttc tcttcggctt aatccagccc     931
gggtccccgg gtgggggtgg aggtgcaga ggaatccaaa ggagtgtcat ctgccaggct      991
cacggagagg agaaactgcg aagtaaatgc ttagacccccc aggggcaagg gtctgagcca   1051
```

```
ctgccgtgcc gcccacaaac tgatttctga aggggaataa ccccaacagg gcgcaagcct    1111
cactattact tgaactttcc aaaacctaga gaggaaaagt gcaatgtatg ttgtatataa    1171
agaggtaact atcaatattt aagtttgttg ctgtcaagat ttttttttgt aacttcaaat    1231
atagagatat ttttgtacgt tatatattgt attaagggca ttttaaaaca attgtattgt    1291
tcccctcccc tctattttaa tatgtgaatg tctcagcgag gtgtaacatt gtttgctgcg    1351
cgaaatgtga gagtgtgtgt gtgtgtgtgc gtgaaagaga gtctggatgc ctcttgggga    1411
agaagaaaac accatatctg tataatctat ttacataaaa tgggtgatat gcgaagtagc    1471
aaaccaataa actgtctcaa tg                                             1493
```

<210> SEQ ID NO 4
<211> LENGTH: 188
<212> TYPE: PRT
<213> ORGANISM: Sus scrofa

<400> SEQUENCE: 4

```
Met Lys Leu Val Pro Val Ala Leu Met Tyr Leu Gly Ser Leu Ala Phe
            -90                 -85                 -80

Leu Gly Ala Asp Thr Ala Arg Leu Asp Val Ala Ala Glu Phe Arg Lys
        -75                 -70                 -65

Lys Trp Asn Lys Trp Ala Leu Ser Arg Gly Lys Arg Glu Leu Arg Leu
    -60                 -55                 -50

Ser Ser Ser Tyr Pro Thr Gly Ile Ala Asp Leu Lys Ala Gly Pro Ala
        -45                 -40                 -35

Gln Thr Val Ile Arg Pro Gln Asp Val Lys Gly Ser Ser Arg Ser Pro
-30                 -25                 -20                 -15

Gln Ala Ser Ile Pro Asp Ala Ala Arg Ile Arg Val Lys Arg Tyr Arg
                -10                  -5                  -1    1

Gln Ser Met Asn Asn Phe Gln Gly Leu Arg Ser Phe Gly Cys Arg Phe
                 5                  10                  15

Gly Thr Cys Thr Val Gln Lys Leu Ala His Gln Ile Tyr Gln Phe Thr
                20                  25                  30

Asp Lys Asp Lys Asp Gly Val Ala Pro Arg Ser Lys Ile Ser Pro Gln
 35                  40                  45                  50

Gly Tyr Gly Arg Arg Arg Arg Ser Leu Pro Glu Ala Ser Leu Gly
                    55                  60                  65

Arg Thr Leu Arg Ser Gln Glu Pro Gln Ala His Gly Ala Pro Ala Ser
                70                  75                  80

Pro Ala His Gln Val Leu Ala Thr Leu Phe Arg Ile
                85                  90
```

<210> SEQ ID NO 5
<211> LENGTH: 1376
<212> TYPE: DNA
<213> ORGANISM: Rattus norvegicus
<220> FEATURE:
<221> NAME/KEY: CDS
<222> LOCATION: (154)..(708)
<221> NAME/KEY: mat peptide
<222> LOCATION: (433)..(582)

<400> SEQUENCE: 5

```
tccagccttt accgctcctg gtttctcggc ttctcatcgc agtcagtctt ggactttgcg    60
ggttttgccg ctgtcagaag gacgtctcgg acttctgct tcaagtgctt gacaactcac    120
cctttcagca gggtatcgga gcatcgctac aga atg aag ctg gtt tcc atc gcc   174
```

```
                Met Lys Leu Val Ser Ile Ala
                                -90
ctg atg tta ttg ggt tcg ctc gcc gtt ctc ggc gcg gac acc gca cgg      222
Leu Met Leu Leu Gly Ser Leu Ala Val Leu Gly Ala Asp Thr Ala Arg
    -85                 -80                 -75 ctc gac act tcc tcg cag ttc cga aag aag tgg aat aag tgg gcg cta      270
Leu Asp Thr Ser Ser Gln Phe Arg Lys Lys Trp Asn Lys Trp Ala Leu
-70                 -65                 -60                 -55 agt cgt ggg aag agg gaa cta caa gcg tcc agc agc tac cct acg ggg      318
Ser Arg Gly Lys Arg Glu Leu Gln Ala Ser Ser Ser Tyr Pro Thr Gly
                -50                 -45                 -40 ctc gtt gat gag aag aca gtc ccg acc cag act ctt ggg ctc cag gac      366
Leu Val Asp Glu Lys Thr Val Pro Thr Gln Thr Leu Gly Leu Gln Asp
            -35                 -30                 -25 aag cag agc acg tct agc acc cca caa gcc agc act cag agc aca gcc      414
Lys Gln Ser Thr Ser Ser Thr Pro Gln Ala Ser Thr Gln Ser Thr Ala
        -20                 -15                 -10 cac att cga gtc aaa cgc tac cgc cag agc atg aac cag ggg tcc cgc      462
His Ile Arg Val Lys Arg Tyr Arg Gln Ser Met Asn Gln Gly Ser Arg
    -5              -1   1               5                  10 agc act gga tgc cgc ttt ggg acc tgc aca atg cag aaa ctg gct cac      510
Ser Thr Gly Cys Arg Phe Gly Thr Cys Thr Met Gln Lys Leu Ala His
                15                  20                  25 cag atc tac cag ttt aca gac aaa gac aag gac ggc atg gcc ccc aga      558
Gln Ile Tyr Gln Phe Thr Asp Lys Asp Lys Asp Gly Met Ala Pro Arg
            30                  35                  40 aac aag atc agc cct caa ggc tat ggc cgc cgg cgc cgg cgt tcc ctg      606
Asn Lys Ile Ser Pro Gln Gly Tyr Gly Arg Arg Arg Arg Ser Leu
        45                  50                  55 cca gag gtc ctc cga gcc cgg act gtg gag tcc tcc cag gag cag aca      654
Pro Glu Val Leu Arg Ala Arg Thr Val Glu Ser Ser Gln Glu Gln Thr
    60                  65                  70 cac tca gct cca gcc tcc ccg gcg cac caa gac atc tcc aga gtc tct      702
His Ser Ala Pro Ala Ser Pro Ala His Gln Asp Ile Ser Arg Val Ser
75                  80                  85                  90 agg tta taggtgcggg tggcagcatt gaacagtcgg gcgagtatcc cattggcgcc        758
Arg Leu tgcggaatca gagagcttcg caccctgagc ggactgagac aatcttgcag agatctgcct     818
ggctgcccct aggggaggca gaggaaccca agatcaagcc aggctcacgt cagaaaccga     878
gaattacagg ctgatactct ctccgggcag gggtctgagc cactgccttg cccgctcata     938
aactggtttt ctcacggggc atacggctca ttacttactt gaactttcca aaacctagcg     998
aggaaaagtg caatgcttgt tatacagcca aagtaacta tcatatttaa gtttgttgat     1058
gtcaagaggt ttttttttt gtaacttcaa atatataga atattttgt acgttatata     1118 ttgtattaag ggcattttaa agcgattata ttgtcacctt cccctatttt aagaagtgaa     1178
tgtctcagca aggtgtaagg ttgtttggtt ccgtgtgtgt gtgtgtgtgt gtgtgtgtgt     1238
gtgtgtgtgt gtgtgtgtaa ggtggagagc gcctgattac cgcctgtgga tgaagaaaaa     1298
acattgtgtc ttctataatc tatttacata aaatatgtga tctgggaaaa agcaaaccaa     1358
taaactgtct caatgctg                                                 1376
```

<210> SEQ ID NO 6
<211> LENGTH: 185
<212> TYPE: PRT
<213> ORGANISM: Rattus norvegicus

<400> SEQUENCE: 6

-continued

```
Met Lys Leu Val Ser Ile Ala Leu Met Leu Leu Gly Ser Leu Ala Val
            -90             -85                 -80

Leu Gly Ala Asp Thr Ala Arg Leu Asp Thr Ser Ser Gln Phe Arg Lys
        -75             -70                 -65

Lys Trp Asn Lys Trp Ala Leu Ser Arg Gly Lys Arg Glu Leu Gln Ala
    -60             -55                 -50

Ser Ser Ser Tyr Pro Thr Gly Leu Val Asp Glu Lys Thr Val Pro Thr
-45             -40                 -35                     -30

Gln Thr Leu Gly Leu Gln Asp Lys Gln Ser Thr Ser Ser Thr Pro Gln
            -25                 -20                 -15

Ala Ser Thr Gln Ser Thr Ala His Ile Arg Val Lys Arg Tyr Arg Gln
            -10              -5                 -1   1

Ser Met Asn Gln Gly Ser Arg Ser Thr Gly Cys Arg Phe Gly Thr Cys
     5               10                 15

Thr Met Gln Lys Leu Ala His Gln Ile Tyr Gln Phe Thr Asp Lys Asp
 20              25              30                      35

Lys Asp Gly Met Ala Pro Arg Asn Lys Ile Ser Pro Gln Gly Tyr Gly
             40              45                      50

Arg Arg Arg Arg Arg Ser Leu Pro Glu Val Leu Arg Ala Arg Thr Val
             55              60                  65

Glu Ser Ser Gln Glu Gln Thr His Ser Ala Pro Ala Ser Pro Ala His
         70              75                 80

Gln Asp Ile Ser Arg Val Ser Arg Leu
     85              90
```